Figure 1:
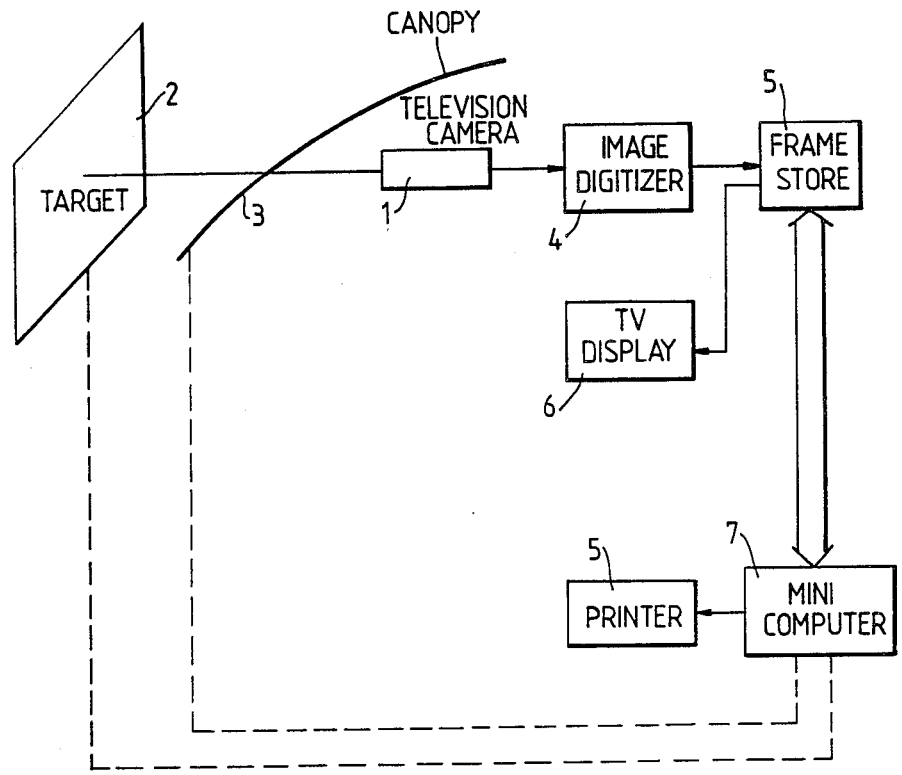

United States Patent [19]

Kalawsky

[11] Patent Number: 4,776,692

[45] Date of Patent: Oct. 11, 1988

[54] TESTING LIGHT TRANSMITTING ARTICLES

[75] Inventor: Roy S. Kalawsky, Brough, England

[73] Assignee: British Aerospace Public Limited Company, London, England

[21] Appl. No.: 779,572

[22] Filed: Sep. 24, 1985

[30] Foreign Application Priority Data

Sep. 24, 1984 [GB] United Kingdom ............... 8424074

[51] Int. Cl.⁴ .................... G01N 21/41; G01N 21/88
[52] U.S. Cl. .................................................. 356/239
[58] Field of Search ............ 356/237, 239, 240, 32–35, 356/71, 364–370

[56] References Cited

U.S. PATENT DOCUMENTS

| | | | |
|---|---|---|---|
| 2,871,756 | 2/1959 | Graves et al. | 356/239 |
| 3,992,571 | 11/1976 | Garlick et al. | 358/81 |
| 4,249,823 | 2/1981 | Task | 356/239 X |
| 4,299,482 | 11/1981 | Task | 356/124 |
| 4,310,242 | 1/1982 | Genco et al. | 356/239 X |
| 4,398,822 | 8/1983 | Task | 356/239 |
| 4,461,570 | 7/1984 | Task et al. | 356/239 |
| 4,641,570 | 2/1987 | Futamura et al. | 92/71 |
| 4,647,197 | 3/1987 | Kitaya et al. | 356/239 |

FOREIGN PATENT DOCUMENTS

| | | | |
|---|---|---|---|
| 2310763 | 9/1974 | Fed. Rep. of Germany | |
| 0200141 | 11/1983 | Japan | 356/239 |
| 1472854 | 5/1977 | United Kingdom | |

Primary Examiner—Eugene R. LaRoche
Assistant Examiner—David Mis
Attorney, Agent, or Firm—Cushman, Darby & Cushman

[57] ABSTRACT

A disclosed canopy testing using an area imaging device, e.g. a T.V. camera, to view a scene, a cross-hatch pattern say, through the canopy. The viewed image is digitized and stored and a computer evaluates the target image by comparing the apparent positions of its features with their real positions and/or by sensing deviations from straightness of the pattern lines. In a development, a polarimeter or polarization sensitive camera is used to test for hazing and curvature defects.

12 Claims, 1 Drawing Sheet

TESTING LIGHT TRANSMITTING ARTICLES

This invention relates to a method and system for testing the optical quality of light transmitting articles. More particularly, but not exclusively, it relates to the evaluation of aircraft transparencies, such as cockpit canopies, with respect to the optical distortion caused by them.

Aircraft cockpit canopies can comprise manufacturing irregularities which produce localised distortion of the view seen through them. Thus, prismatic errors or localised variation in surface parallelism can produce angular deviation between the true and observed positions of an object seen through the canopy. The problem is more acute for the curved canopies having low inclinations to the horizontal which are fitted to modern high speed aircraft—with these, the angular deviation errors may vary widely with the angle of observation and the pilot's eye position. They can also introduce so-called binocular disparity effects.

At present, the evaluation of aircraft cockpit canopies is often done subjectively—for example, an operator may simply look at a grid pattern through the canopy and either accept or reject the canopy in dependence upon the degree of optical distortion which he notices.

To achieve a more objective evaluation, it has been proposed to project a point or small patch light source through the canopy to a lens and beam-splitter combination which forms respective images on two linear imaging arrays. Initially, ie without the canopy present, the projector and receiver assembly are aligned so that the images are positioned accurately at the centre of each linear array. The canopy is then placed in position and any optical aberration at the point on the canopy through which the image is projected may cause the image to be displaced from the centre of one or both arrays—the arrays are positioned of course so that they measure horizontal and vertical displacement, respectively, of the apparent position of the course. The array outputs are fed via a selector switch to a display unit which, by the position of a spot of light along an elongate display area, shows up any displacement of the projected image from the centre of the selected array. This is a point testing technique—after the test of a particular point of the canopy, the canopy is moved to test another point and so on. This takes time and requires care by a specially trained operator—also, since it requires that the two arrays be correctly positioned relative to the beam-splitter and projector, the initial alignment of the apparatus may be difficult to achieve.

Accordingly, it is an object of the invention to provide an objective test method and apparatus which tests a whole area or even the whole of an aircraft cockpit canopy at one go and which further is relatively more easy to set up and carry out than the above-mentioned proposal.

According to one aspect of the invention, there is provided a method of testing the optical quality of a light transmitting article; the method comprising using an image sensor to form a signal representative of an image of a two-dimensional pattern viewed through the article to be tested, storing a series of digital signals representative of respective pixels of said image in a memory and using a computer means connected to said memory to evaluate said digital signals to sense the presence in said image of predetermined features of the pattern and to calculate deviations in shape and/or position of said features due to the presence of said article.

According to a second aspect of the invention, there is provided apparatus for testing the optical quality of a light transmitting article, the apparatus comprising a member bearing a two-dimensional target pattern, image sensor means positioned for viewing said pattern, support means for supporting said article between said pattern and said image sensor means, digitiser means connected to said image sensor means for forming a series of digital signals representative or respective pixels of the image received by the sensor means, frame store means connected to the digitiser means for storing said digital signal, and computer means connected to the frame-store means and operable to evaluate said signals and to calculate deviation in shape and/or position of predetermined features of the pattern due to the presence of said article.

According to a third aspect of the present invention, there is provided a method for testing the optical quality of a light transmitting article, the method comprising using an area-imaging device to form a video signal indicative of a scene as viewed by the device through said article, and using computer means to check said video signal against parameters indicative of the view which would be seen by said device if the article were not present and to produce via output means connected to the computer an indication of discrepancies between the video signal and said parameters.

Said parameters can be embodied in stored video signal form by the device with said article absent, or the parameters can comprise calculated data indicative of the view expected to be seen by the device when the article is not present.

Advantageously, said output means comprise a video display monitor upon which the computer is operable to produce a picture of said scene as viewed via the article with said discrepancies indicated by some easily seen variation of the picture. For example, the colour or brightness of the picture may vary with the degree of deviation between the video signal and the parameters.

According to a fourth aspect of the invention, there is provided apparatus for testing the optical quality of a transparent article, the apparatus comprising an area-imaging device for forming a video signal indicative of a scene viewed by the device via said article, computer means for checking said video signal against parameters indicative of the view which would be seen by the device if the article were not present, and output means for making available an indication of any discrepancies between the video signal and said parameters.

In one embodiment of the apparatus to be described herein, a television camera is arranged to view a target scene, comprising a cross-hatch pattern, for example, respectively directly and then via the article to be tested, an aircraft cockpit canopy for example, the camera output being supplied to a 'frame grabber' which digitises one frame of the video signal formed with the canopy not present and then a frame of the signal formed when the canopy is present. The two sets of digital pixel signals are stored in a frame store and the corresponding pixel signals are compared by a digital computer. The magnitudes of any deviations are digitised and used to control the brightness or colour of corresponding elements of a picture produced by a T.V. monitor.

Figure 2:
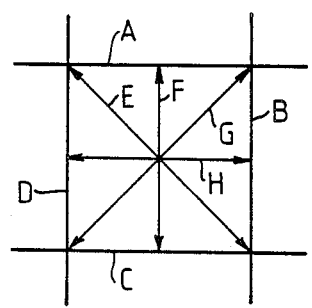
Figure 2:
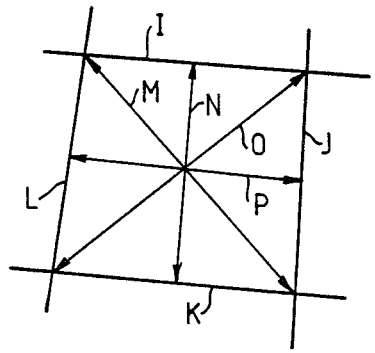

For a better understanding of the invention, reference will be made, by way of example, to the accompanying drawings in which:

FIG. 1 is a block diagram of apparatus for testing an aircraft cockpit canopy, and FIGS. 2A and 2B are diagram for explaining distortion measurement.

The apparatus to be described provides a facility for testing the optical quality of light transmitting articles. The method employs an image sensor to convert the optical distortions, spacial deviations, etc., into a video signal. This video signal is then digitised and stored within a computer. The type and arrangement of the sensor depends on the resolution required for a given application, although the processing techniques remain the same. The optical quality analysis produced by the system can be output in numerical form or with the optical distortions displayed on a visual display monitor, perhaps reinforced by means of colour. The form of output is again dependent on the applications. Provision is made whereby the video signal describing the 'distorted image' can be stored in digital form onto magnetic media, eg, floppy disk.

The simplest arrangement consists of a television camera viewing some optical image, e.g. a cross-hatch or other test pattern. An image is then captured and stored within a digital computer. The item whose optical quality is to be measured, is then placed in front of the camera and a second image is captured and stored in the computer. Once the two images are stored, it is possible to compare them in the digital computer. The magnitudes of any deviations are digitised and used to control the brightness or colour of corresponding elements of a picture produced by a television monitor. FIG. 1 illustrates the apparatus required for testing aircraft transparencies/canopies.

The apparatus comprises a television camera 1 which is set up to view a standard target 2 having some suitable form of cross-hatch pattern formed thereon. With the cockpit canopy 3 not present, an image digitiser 4 connected to the computer, stores one complete frame of the video signal in a framestore 5. Meanwhile, a television display 6 simultaneously displays the contents of the framestore thereby enabling the camera to be focussed correctly if necessary. After an image has been captured, the computer 7 measures the vertical and horizontal spacings of the test pattern so as to produce a mask which is compared with the image obtained via the canopy. For this, the canopy is placed in position such that the camera is at the design eye position. Another image is captured and stored. The mask is then compared with the stored image. The result of the comparison could be displayed in the form of a numerical read-out either on the monitor 6 or on a printer 8.

To produce a permanent test record, the monitor could be photographed, or the contents of the framestore stored on disk, tape or the computer could be programmed to permit the reproduction of say, a greyscale printed copy of the framestore contents on the printer 8.

The television camera 1 could be replaced by some other imaging device, for example charge-coupled device line arrays or area arrays.

Applications of this evaluation system are not limited to measuring the distortions in aircraft transparencies/canopies but to any optical item where the amount of distortion needs to be known.

In a preferred embodiment, instead of comparing images taken with and without the cockpit canopy present, the computer 7 is rendered operable to evaluate an image viewed via the canopy against predetermined parameters programmed into the computer. The target 2 carries a two-dimensional cross-hatch pattern, ie a series of horizontal and vertical straight lines forming a grid made up of squares one of which is shown in FIGS. 2a and 2b. A single image frame from the camera 1 is digitised by digitiser 4 and the resultant series of digital pixel signals are stored in the frame store 5. The computer 7 then addresses the locations of the store 5 so as, in effect, to track across the image in a predetermined direction. For example, the computer might address first the store location containing the signal representative of the pixel at the top, left hand corner of the image, then the location of the pixel which is one row down and one column across, then the location in the third row and third column, and so on, in effect tracking a diagonal line crossing the image from its top, left hand corner. Each time a location is addressed, the computer evaluates the signal therein. Eventually, the computer will reach a location containing a signal representative of the colour of the lines of the pattern, ie it may have found a portion of one of the lines of the pattern or, alternatively, it may just have found some background blemish. To decide which, the computer addresses in turn locations around the line-colour-level containing location. If none of these also contain line-colour-level signals, then it will have been determined that only some sort of blemish has been found. If a second line-colour-level is found, then the computer can track around its location hopefully to find a third line-colour-level and so on. Eventually, the computer will have found a line and by the above-mentioned search process can record its position. The same process also enables the computer to record the positions of all the pattern lines and the positions of the intersections between them. Now, by simply taking each square of the pattern in turn, and subtracting from each other the memory location co-ordinates of appropriate corners and mid-line positions of the square, the computer forms values of the lengths I,J,K,L,M,N,O and P as shown in FIG. 2b. The computer then compares each of these lengths with the known values A,B,C,D,E,F,G, and H respectively for an undistorted square, as shown in FIG. 2a, so as to achieve, for each, an error. Thus a series of error values $E_A = |A-I|$, $E_B = |B-J|$, $E_C = |C-K|$ - - - $E_H = |H-P|$ can be obtained. There can then be assigned a figure of merit to the relevant image area, for example the error values can be simply summed and the magnitude of the sum then represents, inversely, the quality of that portion of the canopy. As will be realised, only a single, correct value of length needs to be available to the computer since, for a square as shown in FIG. 2a, the lengths A,B,C,D,F and H are all equal while G and E are each equal to that length multiplied by half the square root of two. The computer could only measure the lengths A,B,C,D,E and G in FIG. 2a if desired. However, it is preferred to measure the midpoint widths F and H also because it helps to reduce sampling errors—also the distortion may have the effect of making the lines appear curved.

In addition, it may be desireable for the computer to be able to evaluate the errors in each square of the target pattern without any pre-knowledge of the relevant dimensions—this enables the apparatus to be used without the assurance to say a fixed spacing between the camera and target, magnifications of the camera lens, and so on. This can be done because of the above-mentioned relationship between the lengths, ie because of the fact that A,B,C,D,F and H are all equal while G and E each equal the value of say A times half the square root of two, provided the square is undistorted. Thus the computer can simply form error values representing the deviation of each value from a norm derived from the other values and then form an overall merit value as before.

Alternatively, or in addition to what has been described above, the computer 7 may track the lines of the image as described above and, for each, generate an equation representative of the line as a polynomial fit. By then correlating that polynomial with the equation of a straight line, the deviation from straightness of each part of the observed line can be determined. This is a known mathematical technique which, by way of example, is described at section 20.20 ('Regression Analysis' or fitting curved onto straight lines) of the book Advanced Engineering Mathematics by Erwin Kreyszig—4th Edition, 1979, Wiley. Its application to the context of the present invention will be well within the scope of those skilled in the art of computer imge analysis.

Additional signal processing can include edge enhancement to accentuate pattern boundaries, grey-level thresholding (so as to reduce any adverse effects of light reflection from the camera side of the canopy, say). Edge tracking and chain code techniques can be used to determine the mask and image deviations and so on. Zoom lenses could be used to magnify the area of interest if desired with a consequential increase in resolution.

As noted earlier, in some instances, it may be desirable to compute the absolute errors with respect to the geometry of the distorted image. This can be done by relating all measurements to one selected reference point per square.

Having analysed the pattern distortion caused by the canopy, the computer could replace the contents of the frame store 5 by a series of digital signals representing the figures of merit which it has obtained for each portion of the image so that then the monitor 6 will display a picture representative of the optical quality of the canopy. For example, the different merit values could be represented by different colors of the picture, eq the colour red could represent high distortion. Then, if the picture contains too large a proportion of red areas, the operator can easily see that the canopy does not meet requirements. Alternatively, store content could be modified so that the resulting displayed picture still represents the viewed image while at the same time showing the pattern of distortion. For example, the brightness of the display could be modulated in accordance with the target image while its colour (hue) could be varied to highlight areas of distortion. In addition, or alternatively to displaying the distortion pattern, it is preferred that the computer 7 will itself evaluate the canopy as a whole, according to predetermined rules, and the indicate whether or not the canopy is acceptable. The rules are, of course, selectable. For example, it may be that no high distortion portions are permissible, or that some distortion is allowable provided it is confined to certain areas, and so on.

Preferably, the illustrated apparatus is rendered operable so than an image can be taken and evaluated from each design eye position of the pilot. For example, the support for the canopy 3 could be arranged to permit the canopy to be moved relative to the camera 1 and target 2 between respective pre-settable positions horizontally spaced by the distance between the average person's eyes, the camera and canopy being of course set up so that the camera is about where the pilot's head would be relative to the canopy in the eventual aircraft. Then two evaluations can be made, one for each eye position. This preferred feature is important because, as mentioned earlier, the canopies used for modern aircraft can produce effects which vary quite widely from one to the other eye of the pilot.

As a further development of the illustrated apparatus, it can incorporate an unpolarised light source and a polarimeter (not shown) arranged for the polarimeter to receive light from the source after reflection from the canopy and thereby to show up variations in the polarisation effect afforded by different portions of the canopy. Such a polarisation test may better show up effects such as localised hazing of the canopy, ie surface finish defects perhaps caused by polishing of the canopy, curvature deviations, and even residual stresses in the canopy material which may be a source of structural weakness or might produce rainbow effects to the pilot. The polarimeter could take one of the forms disclosed in U.K. Patent Specification No. 1,472,854 for example, ie it can comprise one or two T.V. camera tubes providing respective image signals seen via orthogonally polarising filters—if one camera is used the images are formed successively via a movable filter—along with processing circuits which combines the image singals to form a further signal representative of the polarisation at different points of the image. The polarisation pattern can then be displayed representing variations in polarisation. The camera 1 in drawing FIG. 1 of the present specification could form the or one of the cameras of the polarimeter by being provided with a suitable removable polarising filter (not shown) and by having suitable image signal processing circuits (not shown) able to be switched into the system. Alternatively, instead of providing such circuits, the computer 7 may be able to be programmed to carry out the processing of the two images, taken with orthogonal polarisations so as to form the polarisation pattern image. The polarisation pattern image could then simply be displayed on monitor 6 or, preferably, the computer 7 is operable to evaluate it eg by comparing each resulting pixel signal value stored in store 5 against known acceptable values.

Instead of the T.V. camera 1 or an equivalent solid-state image sensor, a linear imaging array can be used and the area image captured and analysed one line at a time, the canopy or the sensor itself being moved by an appropriate between-line distance following each capture of an image line.

What is claimed is:

1. A method of testing the optical quality of a light transmitting article to be tested, comprising the steps of:
    forming a signal representative of an image of a two-dimensional pattern viewed through the article to be tested;
    storing a series of digital signals representative of respective pixels of said image;
    evaluating said digital signals to sense the presence of predetermined features of the pattern in said image;
    calculating spacial deviations in said features due to the presence of said article; and
    producing an indication of defects in said optical quality which is proportional to a magnitude of said spatial deviations.

2. A method as in claim 1, wherein said calculating spacial deviations step further includes the steps of:
providing information indicative of an image of said two dimensional pattern viewed without said article to be tested; and
comparing said signal representative of an image viewed through said article to be tested with said information indicative of said image without said article to be tested.

3. A method as in claim 1, wherein said calculating spacial deviations step further includes the steps of comparing different portions of said image viewed through said article to be tested with each other in order to derive said spacial deviations.

4. Apparatus for testing the optical quality of a light transmitting article, comprising:
means for presenting a two-dimensional target pattern;
image sensor means positioned for viewing said pattern;
support means for supporting said article between said pattern presenting means and said image sensor means;
digitizer means, connected to said image sensor means, for forming a series of digital signals representative of respective pixels of the image received by the image sensor means;
frame storing means, connected to the digitizer means, for storing said digital signal;
computer means, connected to the frame storing means, for processing said signals to calculate a spacial deviation of predetermined features of the pattern due to the presence of said article; and
indicating means for producing an indication of defects in said optical quality proportional to the magnitude of said spatial deviations.

5. Apparatus according to claim 2, wherein said computer means includes means for image subtracting an undistorted image and the distorted image to produce an indication indicative of said distortion.

6. A system according to claim 5, in which the distorted image is used to derive geometrical relationships between different portions thereof, said geometrical relationships being then applied to the distorted image by one of comparing said geometric relationships with prestored relationships, and polynomial equation fits and their correlations.

7. A system according to claim 5, in which said computer means is also for generating a displayed image containing display elements corresponding to parts of the image for which said deviation has a small value, and means for causing a brightness of said display elements to vary dependent on a distortion of the corresponding parts of said pattern.

8. A system according to claim 7, in which the display elements are displayed in colour.

9. An apparatus as in claim 4, wherein said computer means calculates said spacial deviation by providing a prestored signal indicative of said target pattern viewed without said article, and comparing said prestored digital signal with said digital signal produced by said digitizer means.

10. An apparatus as in claim 4, wherein said computer means calculates said spacial deviation by comparing portions of said digital signal indicative of different portions of said image with one another.

11. A method for testing the optical quality of a light transmitting article, comprising the steps of:
forming a video signal indicative of an optical image as viewed by an area imaging device through said article;
producing first parameters by comparing said video signal against second parameters indicative of a view which would be seen by said device if the article were not present; and
producing an indication of defects in said optical quality proportional to the magnitude of differences between the video signal and said second parameters.

12. Apparatus for testing the optical quality of a transparent article, the apparatus comprising:
an area imaging device for forming a video signal indicative of an optical image viewed by the device via said article;
computer means for checking said video signal against parameters indicative of the view which would be seen by the device if the article were not present; and
output means for providing an indication of discrepancies between the video signal and said parameters proportional to a magnitude of said discrepancies.

* * * * *